(12) United States Patent
Todd

(10) Patent No.: US 11,275,047 B2
(45) Date of Patent: Mar. 15, 2022

(54) ANALYSIS OF A TEST SAMPLE

(71) Applicant: ABER INSTRUMENTS LIMITED, Aberystwyth Dyfed (GB)

(72) Inventor: Robert W. Todd, Aberystwyth Dyfed (GB)

(73) Assignee: ABER INSTRUMENTS LIMITED, Aberystwyth Dyfed (GB)

( * ) Notice: Subject to any disclaimer, the term of this patent is extended or adjusted under 35 U.S.C. 154(b) by 0 days.

(21) Appl. No.: 17/267,395

(22) PCT Filed: Aug. 9, 2019

(86) PCT No.: PCT/GB2019/052246
§ 371 (c)(1),
(2) Date: Feb. 9, 2021

(87) PCT Pub. No.: WO2020/030926
PCT Pub. Date: Feb. 13, 2020

(65) Prior Publication Data
US 2021/0293739 A1 Sep. 23, 2021

(30) Foreign Application Priority Data
Aug. 10, 2018 (GB) ...................... 1813114

(51) Int. Cl.
*G01N 27/22* (2006.01)
*G01N 33/487* (2006.01)
(52) U.S. Cl.
CPC ..... *G01N 27/226* (2013.01); *G01N 33/48735* (2013.01)

(58) Field of Classification Search
CPC ...................... G01N 27/226; G01N 33/48735
See application file for complete search history.

(56) References Cited

U.S. PATENT DOCUMENTS

| 5,269,175 | A | 12/1993 | Chmiel et al. | |
|---|---|---|---|---|
| 8,988,082 | B2* | 3/2015 | Selman | G01N 33/48735 324/649 |
| 2009/0115434 | A1* | 5/2009 | Hirthe | G01N 33/2829 324/693 |
| 2009/0115436 | A1* | 5/2009 | Koehler, III | G01N 33/2829 324/698 |
| 2009/0197243 | A1* | 8/2009 | Rieder | C12Q 1/02 435/5 |
| 2010/0180663 | A1* | 7/2010 | Sun | G01N 33/2888 73/1.02 |

(Continued)

FOREIGN PATENT DOCUMENTS

| DE | 4025841 A1 | 12/1990 |
|---|---|---|
| EP | 1018025 A1 | 7/2000 |

(Continued)

OTHER PUBLICATIONS

Carvell John et al; "Advances in using capacitance based biomass probes in disposable bioreactors and cGMP", Feb. 13, 2014 (Feb. 13, 2014), XP055102097, Retrieved from the Internet: URL:http://www.aberinstruments.com/biotech.

(Continued)

*Primary Examiner* — Alvaro E Fortich
(74) *Attorney, Agent, or Firm* — Dinsmore & Shohl LLP

(57) ABSTRACT

An apparatus is disclosed which uses electrodes to analyse a test sample.

16 Claims, 5 Drawing Sheets

(56) References Cited

U.S. PATENT DOCUMENTS

| | | | | |
|---|---|---|---|---|
| 2011/0316563 A1* | 12/2011 | Davies | ............ | G01N 33/48735 |
| | | | | 324/663 |
| 2012/0007615 A1* | 1/2012 | Todd | ................ | G01N 33/48735 |
| | | | | 324/686 |
| 2012/0068723 A1 | 3/2012 | Sullivan | | |
| 2020/0217778 A1* | 7/2020 | Kotu | ................ | B01L 3/502715 |

FOREIGN PATENT DOCUMENTS

| | | |
|---|---|---|
| EP | 1473359 A1 | 11/2004 |
| EP | 3241892 A1 | 11/2017 |
| GB | 2281396 A | 3/1995 |
| GB | 2481832 A | 1/2012 |
| GB | 2507283 A | 4/2014 |
| GB | 2550120 A | 11/2017 |
| JP | S5913948 A | 1/1984 |
| WO | 0151921 A1 | 7/2001 |
| WO | 0240982 A1 | 5/2002 |
| WO | 2006071800 A1 | 7/2006 |

OTHER PUBLICATIONS

United Kingdom Search Report; United Kingdom Application No. GB1813114.4.
International Search Report dated Nov. 8, 2019; International Application No. PCT/GB2019/052246.

\* cited by examiner

ANALYSIS OF A TEST SAMPLE

CROSS-REFERENCE TO RELATED APPLICATIONS

This application is the U.S. national stage of PCT/GB2019/052246 filed Aug. 9, 2019, which claims priority of United Kingdom patent application 1813114.4 filed Aug. 10, 2018, both of which are hereby incorporated by reference in their entirety.

FIELD OF THE INVENTION

The present invention relates to a method and apparatus of analysis of a test sample. Particularly, but not exclusively, the present invention relates to a method and apparatus which can typically be used to determine the proportion of living cells in a test sample.

BACKGROUND OF THE INVENTION

Capacitance measurement techniques are known for measuring the capacitance (or specific capacitance or dielectric constant) of liquids and suspensions, such as biological cells in ionic aqueous solutions. Known techniques involve introducing metal electrodes into the liquid and applying an excitation signal (usually sinusoidal) and measuring voltage and current using a pair of measurement electrodes. The impedance, conductivity and specific capacitance or permittivity can then be calculated. At high excitation frequencies (greater than about 1 MHz) this is relatively straightforward with simple electrode and circuit configurations. However at lower frequencies, and particularly where the conductivity is high (up to 100 mS/cm or so), the electrode—liquid interface exhibits an impedance which appears in series with the impedance of interest and distorts the measurements.

EP1018025 discloses such a technique for measurement of biomass. This document describes the background to the Beta dispersion and how correction needs to be made for polarisation at measurement electrodes.

Electrode polarisation effects result largely from the charged electrodes attracting around themselves a counter layer of ions which acts electrically as a capacitor/resistor network in series with the suspension that is under measurement investigation. The magnitude of the electrode polarisation effect is largely frequency dependent. To measure the whole of the beta dispersion range (and alpha dispersion range) requires the use of a frequency region in which polarisation of the measuring electrodes can contribute a significant capacitance which has a material distortion on the measured capacitance. This error also varies with time as the electrode surface impedance is not stable and depends upon electrode surface current density.

There have been numerous techniques developed for managing the inherent errors in measurement of the impedance of the test sample. These include the use of a four terminal layout and/or the careful choice of material where the use of gold or platinum electrodes have been found to reduce the impedance between the electrode and test sample. However such electrodes are expensive and there remains some electrode/test sample impedance. A further technique is to increase separation between the electrodes which means the impedance between the electrode and the test sample is less significant in comparison to the impedance of the test sample itself. In order to maximise the electrode separation, alternative probe configurations have been designed for carrying the electrodes whereby for example electrodes are positioned on opposing faces of an insulating finger meaning that the current flow path is around a distal end of the probe finger, or even on opposite sides of a containing vessel such as a fermenter.

Whilst the use of correction algorithms to differentiate between what we wish to measure and the interfering signals and techniques to manage electrode polarisation are to some extent effective, it remains a significant problem as the electrode polarisation impedance is not linear, and is actually variable across the electrode surface and is further variable depending on the current density which in itself may vary. Therefore the effect of electrode polarisation remains a significant issue in analysis of a test sample.

SUMMARY OF THE INVENTION

According to the present invention there is an apparatus for analysis of a test sample comprising:
  a first electrode pair for application of an excitation current to a test sample;
  a measuring arrangement for measuring voltage through the test sample comprising a second electrode pair; and
  a receptacle for receipt of the test sample, where the receptacle comprises a receptacle wall that forms a barrier between the first and second electrode pair and the test sample such that the receptacle wall contacts both the first and second electrode pairs and the test sample when the apparatus is in an operable state.

Thus, the excitation current is driven through the receptacle wall, test sample and receptacle wall between the first and second electrode pair. The voltage is measured through the receptacle wall, test sample and receptacle wall again via the second electrode pair. In an alternative definition having the same meaning, voltage is measured across the test sample.

The four electrode arrangement mitigates against the variability which is inherent in the two terminal arrangement.

The electrodes are therefore be positioned outside the receptacle in operation, and there is no direct contact between the test sample and electrodes in operation.

The test sample may be dielectric.

The measuring arrangement preferably further comprises an arrangement to determine the current and voltage from the first and second electrode pair, and preferably has an extremely high input impedance which makes it possible to measure voltage whilst only causing only a small amount of current flow through the electrode's impedance. The voltage drop across this impedance (which is proportional to electrode current and electrode impedance) is then also very small and causes negligible measurement errors when analysing the test sample.

The receptacle may comprise a flexible material. The receptacle may comprise a polymeric bag, such as for example a blood bag.

The receptacle may be a bio-reactor, and may be configured for a specific cell line. The receptacle may also be a bag fermenter. Such single-use bioreactors have become established in modern biopharmaceutical processes. Such bioreactors may be utilised as examples only for mammalian cell culture, very demanding high cell-density or microcarrier-based processes. Such bioreactors typically comprise a working volume from around 15 ml.

The receptacle may be a bag for storing biomaterial.

There are significant advantages associated with the present invention. Electrode polarisation between electrodes in direct contact with a test sample is non-linear and depends upon current density. A barrier however is more predictable in this regard. In addition, it is beneficial to be able to analyse a test sample whereby contamination is undesirable, and the ability to analyse the test sample without making direct physical contact means that a sample can be analysed without for example removing from a receptacle. For example, a test sample such as blood can be tested for live cells without transferring to another receptacle or opening the receptacle to allow direct contact.

That is to say, the apparatus may enable a test sample to be analysed without direct physical contact with the surface of a measuring electrode. This is advantageous because contamination of the electrodes and the test sample can be avoided and the shelf life of the measuring electrodes can be extended.

The measuring arrangement may measure across any suitable distance of test sample dependent upon the application of the apparatus. For example the receptacle for holding the test sample and electrode size may affect the suitable distance.

The thickness of the receptacle wall is preferably between 0.1 mm and 7 mm, preferably between 0.1 mm and 3 mm, preferably between 0.1 mm and 1 mm, and even more preferably between 0.3 mm and 1 mm. A typical thickness of a receptacle such as a flexible polymeric bioreactor is substantially 0.5 mm.

The receptacle may comprise a span between opposing walls for receipt of the test sample, and the thickness of a receptacle wall is between 4% and 0.005% of the span. Thus, the span is significantly greater than the thickness of the receptacle walls. For example, the wall thickness may comprise 0.5 mm and the span 15 mm, giving a wall thickness of around 3% of the span. In alternative applications the span may be in the order of 1 m with a similar wall thickness, giving a wall thickness of around 0.005% of the span. As the span increases, it will be appreciated that instead of first and second electrodes of each electrode pair being positioned externally of opposing walls, the electrodes may be positioned externally of the same wall. In this case current flows across the test medium between the first electrode pair generally in an arc. Voltage is also measured across the test medium between electrodes external of the same wall. So for example, in the event of a span of 1 m, measurement is not necessarily made across the greatest span.

The receptacle is beneficially non-conductive.

An apparatus according to any preceding claim wherein the apparatus comprises agitation means for agitating the test sample.

The apparatus preferably further comprises a support arrangement for supporting the receptacle, where the support arrangement carries the first and second electrode pair to define a zone wherein the first and second electrode pair contact the receptacle when supported by the support arrangement. The first and second electrode pair are preferably in a fixed location on the support arrangement. The receptacle and support arrangement are preferably configured to cooperate such that there is direct contact between the electrode pairs and the receptacle.

The support arrangement is preferably configured to receive the receptacle into the zone. The zone preferably comprises a receiving zone.

The first electrodes may be positioned such that they are substantially diametrically opposing each other across the receiving zone, and preferably wherein the second electrodes are positioned such that they substantially oppose each other across the receiving zone.

The support arrangement may cradle the receptacle. Alternatively or in addition the support arrangement is arranged to be positioned over the top of the receptacle.

The support arrangement beneficially contains the electrodes of the first and second electrode pair.

The support arrangement may comprise multiple zones comprising a support arrangement array. Thus, multiple receptacles may be received for testing multiple test samples.

In an embodiment there may further be provided means to agitate the receptacle. This causes the test sample to be mixed during testing to prevent settling of the test sample and therefore inaccurate measurement does not occur. The agitation may be caused by an arrangement which rocks the sample so as to cause the sample to have a more even consistency.

The support arrangement may be arranged to cradle the receptacle. This is beneficial in the event that the test sample is supplied in a flexible receptacle. The receptacle may seat onto the support arrangement. The support arrangement may comprise a platform for receipt of the receptacle. The electrodes are preferably positioned such that the receptacle sits onto the electrodes. Therefore, in an operative position the receptacle may sit onto the electrodes. The electrodes may be upwardly facing and preferably outwardly facing.

The support arrangement may comprise a base and sidewalls defining a cavity forming the zone for receipt of the receptacle. The electrodes of each electrode pair are preferably positioned on the sidewalls having exposed electrode surfaces in the cavity. This means that a receptacle containing the test sample may be located into the cavity and the receptacle will be in direct contact with the electrodes. The electrode pair are preferably disposed such that current is passed through the cavity between the electrodes, and voltage is measured across the cavity.

In an embodiment of the invention the receptacle may comprise a base and sidewalls defining a cavity for receipt of the test sample, the sidewalls having an inner and an outer surface, and the electrode pair are disposed on the outer surface. The electrode pair are preferably disposed such that current is passed through the cavity.

In order to optimise the ability to measure the voltage of the test sample through the barrier, it is beneficial to design the electrode pair appropriately. A challenge is to measure an adequate signal without requiring input of too high an excitation voltage. An upper voltage limit may be in the order of 50V. This can in part be achieved through providing a larger contact electrode surface area in contact with the barrier than is typical for electrodes used for direct contact with a test sample.

That said, the efficacy of the apparatus is determined by any one or more of barrier thickness, contact electrode surface area and operational convenience and the shielding of the electrodes from unwanted electrical fields. Any suitable arrangement of electrodes would achieve the advantages set out above.

The contact electrode surface area may be between 1 $cm^2$ and 50 $cm^2$ when the barrier comprises a polymeric bag. However, there is a trade-off between the thickness of the barrier and the contact area. For thin barriers, contact electrode surface may be of the order of square millimetres. Thin barriers may be formed using any suitable technique such as, for example, chemical vapour deposition and may be of the order of microns in thickness.

The first electrode pair each have a barrier contact surface area and the second electrode pair each have a sensing surface area. The second electrode pair may have a sensing surface area less than the barrier contact surface area of the first electrode pair.

The barrier contact surface area of at least one of the first electrode pair and the sensing surface area of at least one of the second electrode pair are separated from each other. The barrier contact surface area of one of the first electrode pair electrodes may be arranged to at least partially surround the sensing surface area of one of the electrodes of the second electrode pair. It will be appreciated that the second of the first electrode pair of electrodes may also be arranged to at least partially surround the sensing surface area of the second electrode of the second electrode pair. One or each of the second electrode pair may be completely surrounded by the corresponding electrode of the first electrode pair.

There is a balance to be struck between maximising the voltage signal to be measured for the input excitation current which is dependent on the spacing between the first electrode pair and also the possibility of direct coupling between the first and second electrode pair. As such, with the relative position of the first and second electrodes of the first and second electrode pair respectively, current driven through the first electrode pair adds to the voltage drop across the second electrode pair which improves measurability. That is to say, the relative positions of the first and second electrodes in the first and second electrode pair can be optimised to maximise the sensed voltage for a given excitation current.

It will be appreciated that as presented herein any of the preferred or optional features for positioning of the electrode pair may also be applicable to the second electrode pair.

One or more shielding arrangements are preferably provided for shielding each of the respective second electrodes from charge resulting from the application of the excitation current by the first electrode pair. This prevents stray current contaminating the signal determined by the measuring arrangement. The second electrodes preferably have a sensing surface area and a non-sensing surface area, and the or each shielding arrangement may be positioned around the non-sensing surface area. The sensing area can be described as area of electrodes that is uncovered, and preferably contacts the receptacle wall in an operable configuration. The or each shielding arrangement is preferably positioned at least partially in the support arrangement to provide a barrier between the first electrodes and second electrodes.

In an embodiment of the invention, the first and the second electrode pairs are arranged to adhere to the receptacle. Accordingly, a user may position the electrodes as required onto a receptacle in desired location. The electrodes may comprise an adhesive material. The electrodes may be carried by a support that may carry one of the electrodes of each pair, and may comprise a second support for carrying the other of the first and second electrode.

The first and second electrode pairs may mountable and demountable to the receptacle.

Also according to the present invention there is an apparatus for analysis of a dielectric test sample, the apparatus comprising:
 a first electrode pair for application of an excitation current to a test sample;
 a measuring arrangement for measuring voltage across a test sample comprising a second electrode pair; and
 a support arrangement for carrying the first and second electrode pair, the support arrangement configured to define a zone to support a receptacle for carrying the test sample such that the receptacle is in communication with the first and second electrode pair when in the zone.

The support arrangement is preferably configured to receive the receptacle into the zone.

The first electrodes are preferably positioned such that they are substantially diametrically opposing each other across the zone, and preferably wherein the second electrodes are positioned such that they substantially oppose each other across the zone.

The support arrangement may be arranged to cradle the receptacle.

The support arrangement may be arranged to be positioned over the top of the receptacle.

The support arrangement may contain the electrodes of the first and second electrode pair.

The support arrangement may comprise multiple zones comprising a support arrangement array.

The apparatus may comprise one or more shielding arrangements for shielding each of the respective second electrodes from charge resulting from the application of the excitation current by the first electrode pair.

The second electrodes may have a sensing surface area and a non-sensing surface area, and the or each shielding arrangement is positioned around the non-sensing surface area.

The or each shielding arrangement may be positioned at least partially in the support arrangement to provide a barrier between the first electrodes and second electrodes.

The test sample may be dielectric.

The first and second electrodes may be stuck onto the receptacle using an adhesive layer.

The support arrangement is beneficially arranged to receive a test sample carrying receptacle. The support arrangement may cradle a test sample carrying receptacle.

According to a further aspect of the invention there is a method of analysing a test sample, the method comprising:
 applying an excitation current to the test sample provided in a receptacle using a first electrode pair and measuring voltage across the test medium using a second electrode pair, wherein the receptacle comprises a receptacle wall that forms a barrier between the first and the second electrode pair and the test sample; and
 determining one or more properties of the test sample derived from the measured voltage.

It will be appreciated that the current flow between the first electrode pair is also beneficially measured and used in determination of the properties of the test sample.

A support arrangement is also preferably provided for supporting the receptacle, where the support arrangement carries the first and second electrode pair to define a zone wherein the first and second electrode pair contact the receptacle when supported by the support arrangement, and the method preferably comprises positioning the receptacle in the zone.

Apparatus and methods are preferably apparatus and methods for measurement of biomass.

BRIEF DESCRIPTION OF THE DRAWINGS

Aspects of the present invention will now be described by way of example only with reference to the accompanying Figures where.

DETAILED DESCRIPTION OF THE PREFERRED EMBODIMENT

Figure 1:
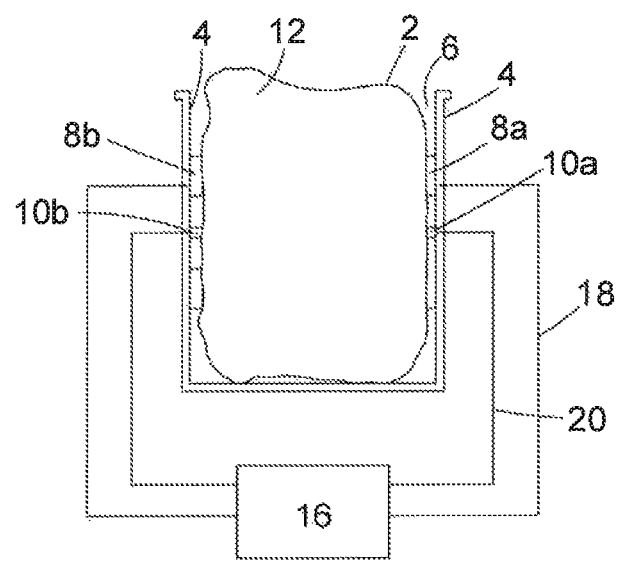
FIG. 1 is a schematic representation of a side view of an illustrative embodiment of the present invention.

Referring to FIG. 1 there is a schematic representation of an illustrative embodiment of the present invention. A receptacle 2 is provided which is illustrated as a flexible bag but may take a solid form which in turn is received into a support arrangement 4 defining a zone in the form of a cavity 6. The receptacle wall forms the barrier between the test sample within the receptacle 2 and the electrodes. A first electrode pair 8a,8b are presented in addition to a measuring arrangement utilising a second electrode pair 10a,10b. The first electrode pair 8a, 8b are arranged to drive current through the test sample 12 provided within the receptacle 2. The current pathway is therefore from electrode 8a, through the receptacle wall, through the test sample, through the receptacle wall on the opposite side of the receptacle and to the opposing electrode 8b. That is to say, no direct physical contact between the electrodes and the test sample takes place.

It will be appreciated that multiple support arrangements 4 may be provided in communication to form an array for testing of multiple samples concurrently.

Figure 5:
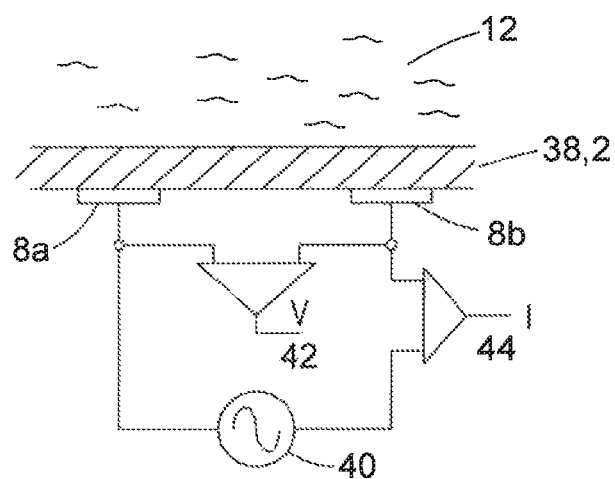
FIG. 5 is a schematic circuit diagram representing the provision of a barrier between the single electrode pair and the test sample, where the voltage is measured across the electrode pair.
Figure 6:
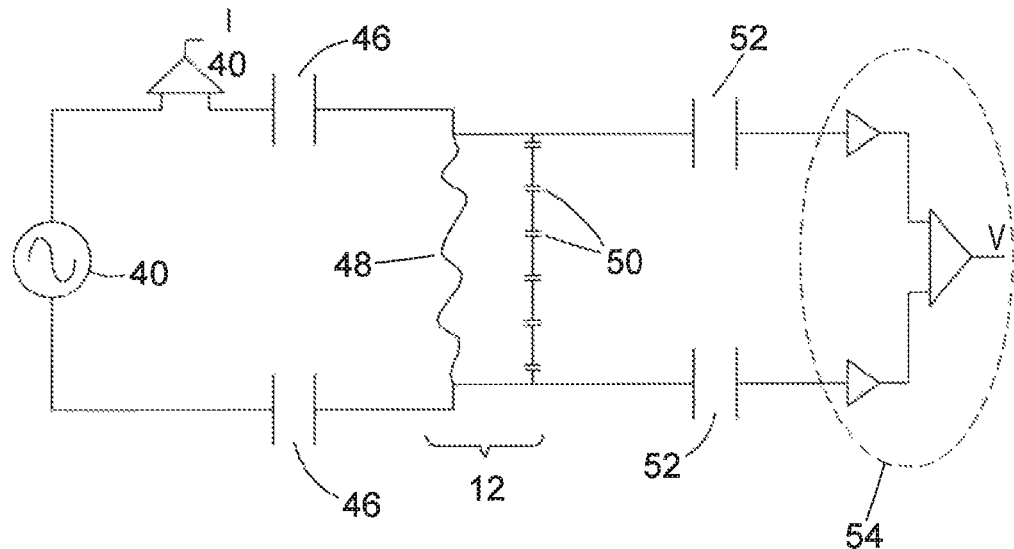
FIG. 6 is a schematic circuit representation of the provision of a barrier between a first electrode pair for supplying current to the test sample and a second electrode pair for measuring voltage across the test sample.

This is also presented schematically in FIGS. 5 and 6. A schematic representation of the electrodes 8 and 10 are presented in FIG. 7.

In the embodiment presented the support arrangement 4 is an insulating material which is a rigid material such as a polymer. The respective electrodes are positioned on the inner surface of the support arrangement walls 14, and preferably oppose one another in order that the test sample is analysed effectively. A means to agitate the test sample such as a rocking device (not shown) for rocking the support arrangement 4 may be provided.

In the embodiment presented separate measuring electrodes 10a,10b are provided to the excitation electrodes 8a, 8b. The measuring arrangement 16 further comprises apparatus to measure the current through the circuit 18 passing through the test sample via the first electrode pair and also the voltage across the second electrode pair 10a, 10b via circuit 20. The voltage drop can be measured from which the specific capacitance determined thereby providing an indication of the amount of live cells within the test sample.

Figure 2:
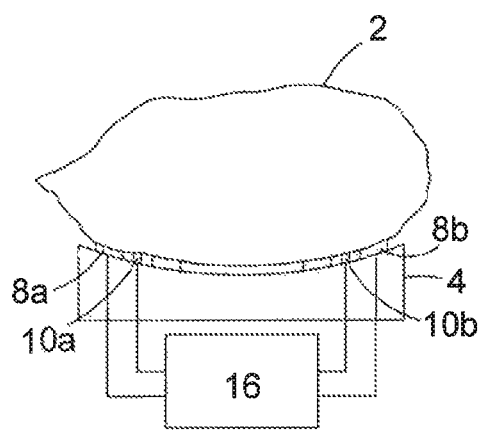
FIG. 2 is a schematic representation of a side view of an illustrative further embodiment of the present invention.

A similar embodiment is presented in FIG. 2, whereby a flexible receptacle 2 is provided and is seated onto a support arrangement 4 having exposed first and second electrode pairs 8, 10. The support arrangement 4 is shown curved to cradle a flexible receptacle 2 in the illustrative embodiment. In this embodiment the electrodes are outwardly facing and communicate with the receptacle 2 in operation and the current flowpath is not across the receptacle 2 but is instead through an arc in the test sample 12. Again, there is no direct contact between the test sample and the electrodes.

Figure 3:
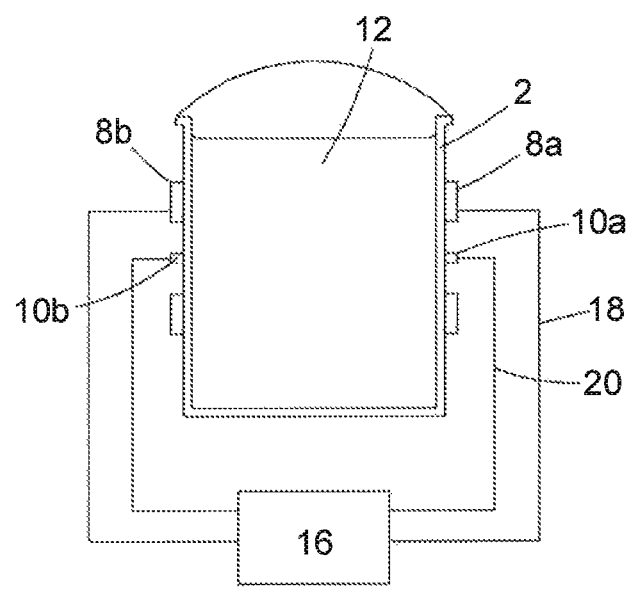
FIG. 3 is a schematic representation of a side view of an illustrative further embodiment of the present invention.

Referring to FIG. 3, the barrier in this embodiment is provided by the wall of the receptacle and the test sample 12 is provided in direct communication with the internal wall of the non-conductive receptacle. The first and, if present, second electrode pair are provided in communication with the opposing side of the receptacle wall. Thus, measurement of the voltage is made through the receptacle wall. The electrodes 8,10 may be carried by a support arrangement to be in contact with the receptacle wall or may be adhered to the receptacle wall. Thus, the method of testing the sample may comprise either positioning a receptacle containing a test sample into communication with the zone of the receptacle in contact with the electrodes 8,10, or alternatively positioning the electrodes onto the receptacle.

Figure 4:
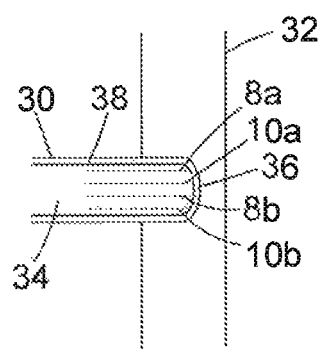
FIG. 4 is a schematic representation of a side view of an illustrative further embodiment of the present invention.

Referring to the embodiment of FIG. 4, a probe 30 is provided for use in the measurement of the concentration of live biomass. In this embodiment the probe 30 is inserted into a test sample which may be carried in, for example, a conduit 32 or a tank or a vessel through which test sample may flow. The probe 30 has an elongate insulating body portion 34 arranged to carry the first 8a,8b and second 10a,10b electrode pairs. As shown in the illustrative embodiment again first and second electrode pairs are represented, although voltage can also be measured across the first electrode pair 8a,8b only. The second electrode 8b of the first electrode pair (and second electrode of the second electrode pair 10b) is shown in dashed lines as is provided on the opposing side of the body portion 34. The elongate body portion 34 has a longitudinal length extending to a tip in a longitudinal axis wherein the first and second electrode pairs extend lengthwise towards the tip 36 in the longitudinal axis. An insulating coating or cover 38 acts as a barrier between the body portion 34, and in particular the electrodes, and the test sample meaning that the probe body is not in direct contact with the test sample. The electrodes may also be positioned along the length of the elongate body portion 34 to form what would resemble rings around the elongate body portion 34.

Referring to FIG. 5 there is a schematic representation of utilising a single electrode pair 8a,8b for input of an excitation current into a test sample and also using the same electrodes 8a,8b for measurement of voltage (in order that voltage drop can be determined) across the test sample. The schematic diagram shows the test sample 12 and barrier which may be in the form of a wall of a receptacle 2 or a coating 38 on a probe. Electrode pair 8a,8b are utilised to input excitation current from source 40. Voltage is measured across the electrodes 8a,8b at reference numeral 42 and current is amplified and measured at numeral 44. In such an embodiment it can be difficult to achieve accurate measurement of current and voltage if there is any change associated with the receptacle/barrier 2 such as movement relative to the electrodes 8a,8b.

Referring to FIG. 6, a schematic representation is made of the circuit from the perspective of current input and voltage measured. In this alternative embodiment, a first electrode pair is utilised for input current to the test sample, and a second electrode pair is utilised for measurement. The AC power source 40 supplies current through the barrier represented by capacitors 46 and through the test sample 12. The test sample 12 can be represented as resistor-capacitor network 50. The small capacitors are indicative of live cells due to the live cells not becoming polarised under the applied current. Measurement of current is made using the left side of the circuit via the test sample 48 and the right side of the circuit representative of the voltage measurement side, where the voltage is measured through the barrier 46 as schematically represented as large capacitors 52 compared to those of the cells as represented by capacitors 50. The voltage is measured through a differential amplifier 54 with a high input impedance. This is necessary to enable measure of what is effectively an extremely small capacitance of the cells. Measurement is being made of the voltage through the receptacle meaning an extremely small phase shift is measured. If measured without utilising such a differential amplifier with high input impedance then the input current to the measuring device would cause a phase shift thereby significantly affecting measurement ability. The provision of an 'infinite' impedance differential amplifier is therefore used for measurement. The circuit will also need to have appropriate compensation for the common mode rejection of the amplifier. The common mode rejection can be achieved using any known means.

Figure 7:
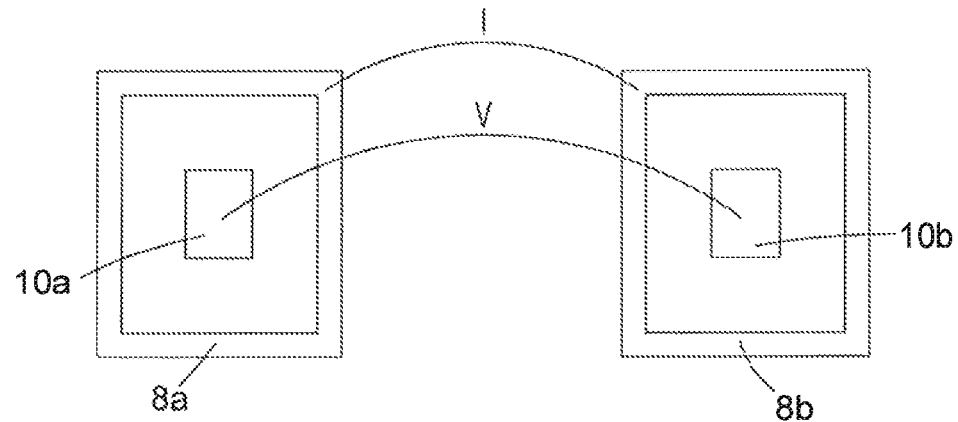
FIG. 7 is a schematic illustrative representation of an electrode configuration for application with any of the embodiments presented.

Referring now to FIG. 7, there is a schematic representation in plan view of a first 8a,8b and second 10a,10b electrode pair. The first electrode pair 8a,8b each have a barrier contact surface area 8c, 8d which in an operable configuration communicate with the receptacle, and the second electrode pair 10a, 10b each have a sensing surface area 10c,10d also for communicating with the receptacle, where the contact surfaces are presented in FIG. 8. The second electrode pair 10a,10b may comprise a sensing surface area less than the barrier contact surface area of the first electrode pair. The barrier contact surface area of one of the first electrode pair electrodes is shown arranged to surround the sensing surface area of one of the electrodes of the second electrode pair. The second of the first electrode pair of electrodes is also arranged to surround the sensing surface area of the second electrode of the second electrode pair. As an illustrative embodiment only, the electrode dimensions 8a and 8b is 50 mm×100 mm with a width of 10 mm. The electrode dimensions of 10a and 10b are 10 mm×50 mm. The span between the electrodes is 12 mm.

Figure 8:
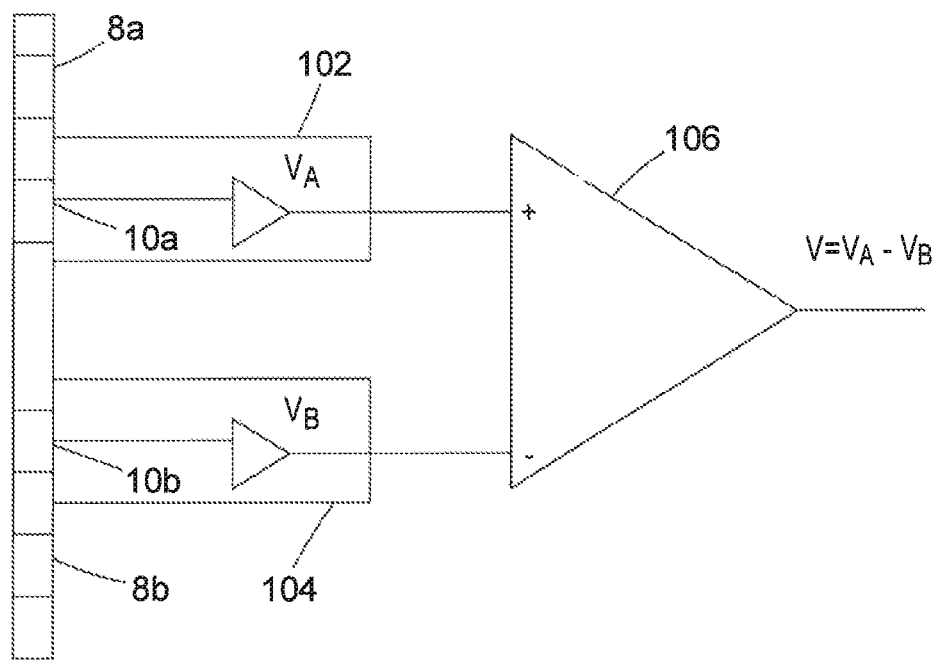
FIG. 8 is a schematic illustration of an electrode configuration whereby the measuring electrodes are shielded by metal enclosures to prevent contamination from the electrode pair in accordance with any embodiment.

FIG. 8 illustrates an embodiment where metal shield members 102 and 104 are used to prevent contamination of stray electrical charge from electrodes 8a and 8b into the electrodes 10a and 10b before the determination of the voltage V in the differential amplifier 106. The electrodes 8a, 8b, 10a and 10b are carried by a support arrangement 4 such that sensing surface areas 10c and 10d of respective electrodes 10a and 10b and the barrier contact areas 8c and 8d of the electrodes 8a and 8b communicate with the receptacle 2 in operation. The shield members 102 and 104 enclose the electrodes 10a and 10b so that as current flows between electrodes 8a and 8b stray current contaminating the signal measured at the differential amplifier 106 is prevented. The shield members 102 and 104 are grounded so that they do not transfer interfering voltage to electrodes 10a and 10b.

Figure 9:
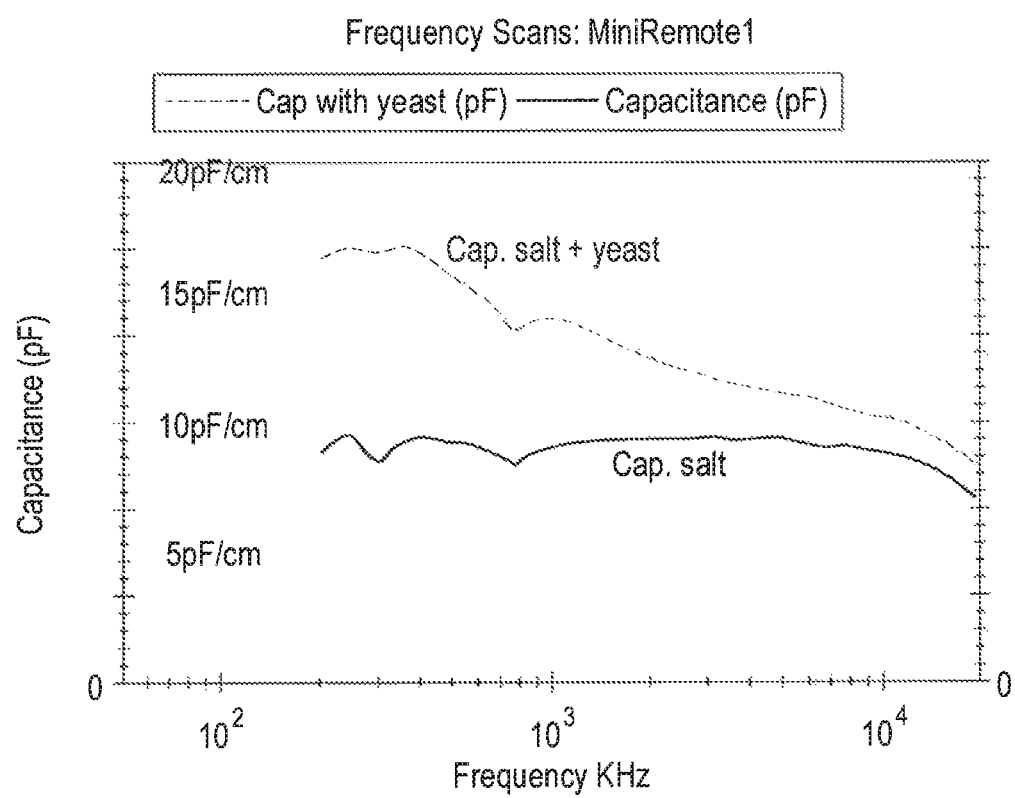
FIG. 9 is a schematic illustration of the capacitance values that are realised for different test samples using an illustrative embodiment of the present invention.

FIG. 9 illustrates the capacitance values that are obtained for first and second test samples in accordance with an illustrative embodiment of the invention comprising respectively water mixed with salt and yeast (dashed lines) and water mixed with just salt (solid lines). It will be evident that different capacitance values are realised at different frequencies for each respective test sample. Measurements for plotting of the lines in FIG. 9 were made using the electrode configuration as presented in FIG. 7, with a span between electrodes of 12 mm and a receptacle with wall thickness of 0.5 mm.

That is to say, the measuring apparatus 16 receives the voltage measurements from the measuring electrodes 10a and 10b and uses them to determine the capacitance of the test sample. The capacitance is indicative of the contents of the test sample and in FIG. 9, the difference between water mixed with salt and water mixed with salt and yeast is illustrative of the effect that the presence of yeast over a larger range of frequencies.

Aspects of the present invention have been described by way of example only and it will be appreciated to the skilled addressee that modifications and variations may be made without departing from the scope of protection afforded by the appended claims.

The invention claimed is:

1. An apparatus for analysis of a test sample comprising:
   a first electrode pair for application of an excitation current to a test sample;
   a measuring arrangement for measuring voltage through the test sample comprising a second electrode pair, the measuring arrangement being further configured to receive the measured voltage and use the measured voltage to determine the capacitance of the test sample; and
   a receptacle for receipt of the test sample, where the receptacle comprises a receptacle wall that forms a barrier between the first and second electrode pair and the test sample such that the receptacle wall contacts both the first and second electrode pairs and the test sample when the apparatus is in an operable state;
   one or more shielding arrangements for shielding each of the respective second electrodes from charge resulting from the application of the excitation current by the first electrode pair; and
   a support arrangement for supporting the receptacle, where the support arrangement carries the first and second electrode pair to define a zone wherein the first and second electrode pair contact the receptacle when supported by the support arrangement, and wherein the support arrangement is configured to receive the receptacle into the zone.

2. The apparatus according to claim 1, wherein the barrier comprises a flexible material.

3. The apparatus according to claim 2, wherein the receptacle is a polymeric bag.

4. The apparatus according to claim 3, wherein the receptacle is a bioreactor.

5. The apparatus according to claim 1, wherein a thickness of the receptacle wall is between 0.1 mm (millimeter) and 7 mm, or between 0.1 mm and 3 mm, or between 0.1 mm and 1 mm, or 0.5 mm.

6. The apparatus according to claim 1, wherein the receptacle comprises a span between opposing walls for receipt of the test sample, and a thickness of a wall is between 4% and 0.005% of the span.

7. The apparatus according to claim 1, wherein the apparatus further comprises agitation means for agitating the test sample.

8. The apparatus according to claim 1, wherein the first electrodes are positioned such that they are substantially diametrically opposing each other across the zone, and wherein the second electrodes are positioned such that they substantially oppose each other across the zone.

9. The apparatus according to claim 1, wherein the support arrangement is arranged to cradle the receptacle.

10. The apparatus according to claim 1, wherein the support arrangement is arranged to be positioned over the top of the test sample.

11. The apparatus according to claim 1, the support arrangement contains the electrodes of the first and second electrode pair.

12. The apparatus according to claim 1, wherein the support arrangement comprises multiple zones comprise a support arrangement array.

13. The apparatus according to claim 1, wherein the second electrodes have a sensing surface area and a non-sensing surface area, and the or each shielding arrangement is positioned around the non-sensing surface area.

14. The apparatus according to claim 13, wherein the or each shielding arrangement is positioned at least partially in the support arrangement to provide a barrier between the first electrodes and second electrodes.

15. The apparatus according to claim 1, wherein:
the first and the second electrode pairs are arranged to adhere to the receptacle; and/or
the first and second electrode pairs are mountable and demountable to the receptacle; and/or
the voltage is measured through a differential amplifier with a high input impedance;
and wherein the apparatus is arranged to have appropriate compensation for common mode rejection of the differential amplifier.

16. A method of analysing a test sample, the method comprising:
applying an excitation current to the test sample provided in a receptacle using a first electrode pair and measuring voltage across the test medium using a second electrode pair wherein the receptacle comprises a receptacle wall that forms a barrier between the first and the second electrode pair and the test sample and where one or more shielding arrangements shield each of the respective second electrodes from charge resulting from the application of the excitation current by the first electrode pair;
providing a support arrangement for supporting the receptacle, where the support arrangement carries the first and second electrode pair to define a zone wherein the first and second electrode pair contact the receptacle when supported by the support arrangement, and the method further comprising positioning the receptacle in the zone; and
determining one or more properties of the test sample derived from the measured voltage, wherein at least one of the properties comprises capacitance.

* * * * *